US010548754B1

(12) United States Patent
Paulos

(10) Patent No.: US 10,548,754 B1
(45) Date of Patent: *Feb. 4, 2020

(54) MAGNET ASSISTED ORTHOTIC BRACE

(71) Applicant: THE LONNIE AND SHANNON PAULOS TRUST (AS AMENDED AND RESTATED), Salt Lake City, UT (US)

(72) Inventor: Lonnie E. Paulos, Salt Lake City, UT (US)

(73) Assignee: THE LONNIE AND SHANNON PAULOS TRUST (AS AMENDED AND RESTATED), Salt Lake City, UT (US)

( * ) Notice: Subject to any disclaimer, the term of this patent is extended or adjusted under 35 U.S.C. 154(b) by 360 days.

This patent is subject to a terminal disclaimer.

(21) Appl. No.: 15/357,130

(22) Filed: Nov. 21, 2016

Related U.S. Application Data

(63) Continuation of application No. 14/604,982, filed on Jan. 26, 2015, now Pat. No. 9,522,076, which is a
(Continued)

(51) Int. Cl.
*A61F 5/00* (2006.01)
*A61F 5/01* (2006.01)

(52) U.S. Cl.
CPC .......... *A61F 5/0102* (2013.01); *A61F 5/0125* (2013.01); *A61F 2005/0139* (2013.01)

(58) Field of Classification Search
CPC . A61B 17/0469; A61B 17/3468; A61B 17/00; A61B 17/00234; A61B 17/0401; A61B 2017/0086; A61B 2017/0464; A61B 2017/00243; A61B 2017/00477; A61B 2017/00557; A61B 2017/00783; A61B 17/29; A61B 2017/00398; A61B 34/30;
(Continued)

(56) References Cited

U.S. PATENT DOCUMENTS 6,296,595 B1 * 10/2001 Stark ................. A61B 5/1071
482/8
8,939,924 B1 * 1/2015 Paulos ................ A61F 5/0102
602/16
(Continued)

*Primary Examiner* — Kim M Lewis
(74) *Attorney, Agent, or Firm* — John Brooks Law LLC; John J. Brooks, III

(57) ABSTRACT

An orthotic brace and brace hinge are disclosed where the brace hinge comprises a multiple hinge elements and at least one hinge element having a magnetic field that provides a magnetic force urging one hinge elements in a pre-determined direction. Embodiments generally utilize magnetic forces to stabilize, influence and/or maintain adjacent joint portions in pre-determined desired relationships and for constraining motion and/or rotation of the joint portions. Through the use of the repelling and attracting forces of magnets, mechanical forces in the brace and brace hinge can be replaced or supplemented to reduce the force put on joint bones, to influence the bones so that the joint is biased into certain positions or to apply different forces through different points of joint flexion. Embodiments of braces with magnetic fields on other brace elements are also disclosed.

18 Claims, 11 Drawing Sheets

Related U.S. Application Data continuation of application No. 12/781,212, filed on May 17, 2010, now Pat. No. 8,939,924.

(60) Provisional application No. 61/179,359, filed on May 18, 2009.

(58) Field of Classification Search
CPC ........ A61B 17/105; A61B 2017/00221; A61B 2017/00734; A61B 2017/2927; A61B 2090/0811; A61B 17/0482; A61B 17/0483; A61B 17/1285; A61B 18/1206; A61B 18/1445; A61B 2017/00017; A61B 2017/00039; A61B 2017/00115; A61B 2017/00464; A61B 2017/2903; A61B 2018/00577; A61B 2018/0063; A61B 2018/00875; A61B 2018/1253; A61B 2018/126; A61B 90/98; A61B 17/0491; A61B 17/06004; A61B 17/06066; A61B 17/06114; A61B 17/06133; A61B 17/062; A61B 17/0625; A61B 17/068; A61B 17/07207; A61B 17/128; A61B 17/282; A61B 17/2833; A61B 17/2841; A61B 17/285; A61B 17/2909; A61B 17/295; A61B 17/3201; A61B 2017/00026; A61B 2017/0003; A61B 2017/00057; A61B 2017/00061; A61B 2017/00075; A61B 2017/00119; A61B 2017/00128; A61B 2017/00212; A61B 2017/00367; A61B 2017/00407; A61B 2017/00438; A61B 2017/00526; A61B 2017/06052; A61B 2017/06076; A61B 2017/07271; A61B 2017/2845; A61B 2017/2902; A61B 2017/2911; A61B 2017/2923; A61B 2017/2925; A61B 2017/2945; A61B 2018/00077; A61B 2018/00083; A61B 2018/00208; A61B 2018/00595; A61B 2018/00601; A61B 2018/00696; A61B 2018/00702; A61B 2018/00708; A61B 2018/0072; A61B 2018/00767; A61B 2018/00827; A61B 2018/00892; A61B 2018/1266; A61B 2018/1452; A61B 2018/1457; A61B 2018/146; A61B 34/20; A61B 90/03; A61B 17/072; A61B 17/320068; A61B 17/3403; A61B 17/842; A61B 2017/00022; A61B 2017/00309; A61B 2017/00314; A61B 2017/0046; A61B 2017/07278; A61B 2017/2908; A61B 2017/2926; A61B 2034/107; A61B 2090/064; A61B 34/10; A61B 134/35; A61B 34/37; A61B 17/00491; A61B 17/0218; A61B 117/0467; A61B 17/0485; A61B 17/0487; A61B 17/083; A61B 17/122; A61B 17/1222; A61B 17/1615; A61B 17/1637; A61B 17/1671; A61B 17/1675; A61B 17/17; A61B 17/1757; A61B 17/3401; A61B 17/3421; A61B 17/3423; A61B 17/683; A61B 17/7013; A61B 17/7053; A61B 17/7083; A61B 17/82; A61B 17/8869; A61B 18/02; A61B 18/06; A61B 18/1442; A61B 18/1492; A61B 18/16; A61B 18/1815; A61B 18/22; A61B 18/24; A61B 1/00078; A61B 1/00087; A61B 1/00096; A61B 1/00135; A61B 1/0014; A61B 1/00179; A61B 1/0051; A61B 1/015; A61B 1/018; A61B 1/05; A61B 2017/00004; A61B 2017/00106; A61B 2017/00123; A61B 2017/00199; A61B 2017/00287; A61B 2017/00292; A61B 2017/00296; A61B 2017/00336; A61B 2017/0034; A61B 2017/00402; A61B 2017/00473; A61B 2017/00566; A61B 2017/00818; A61B 2017/00876; A61B 2017/00893; A61B 2017/00898; A61B 2017/0404; A61B 2017/0409; A61B 2017/0417
USPC .......................................................... 602/16
See application file for complete search history.

(56) References Cited

U.S. PATENT DOCUMENTS 9,522,076 B1 * 12/2016 Paulos ................. A61F 5/0102
2008/0097269 A1 * 4/2008 Weinberg ................. A61F 2/68
602/16

* cited by examiner

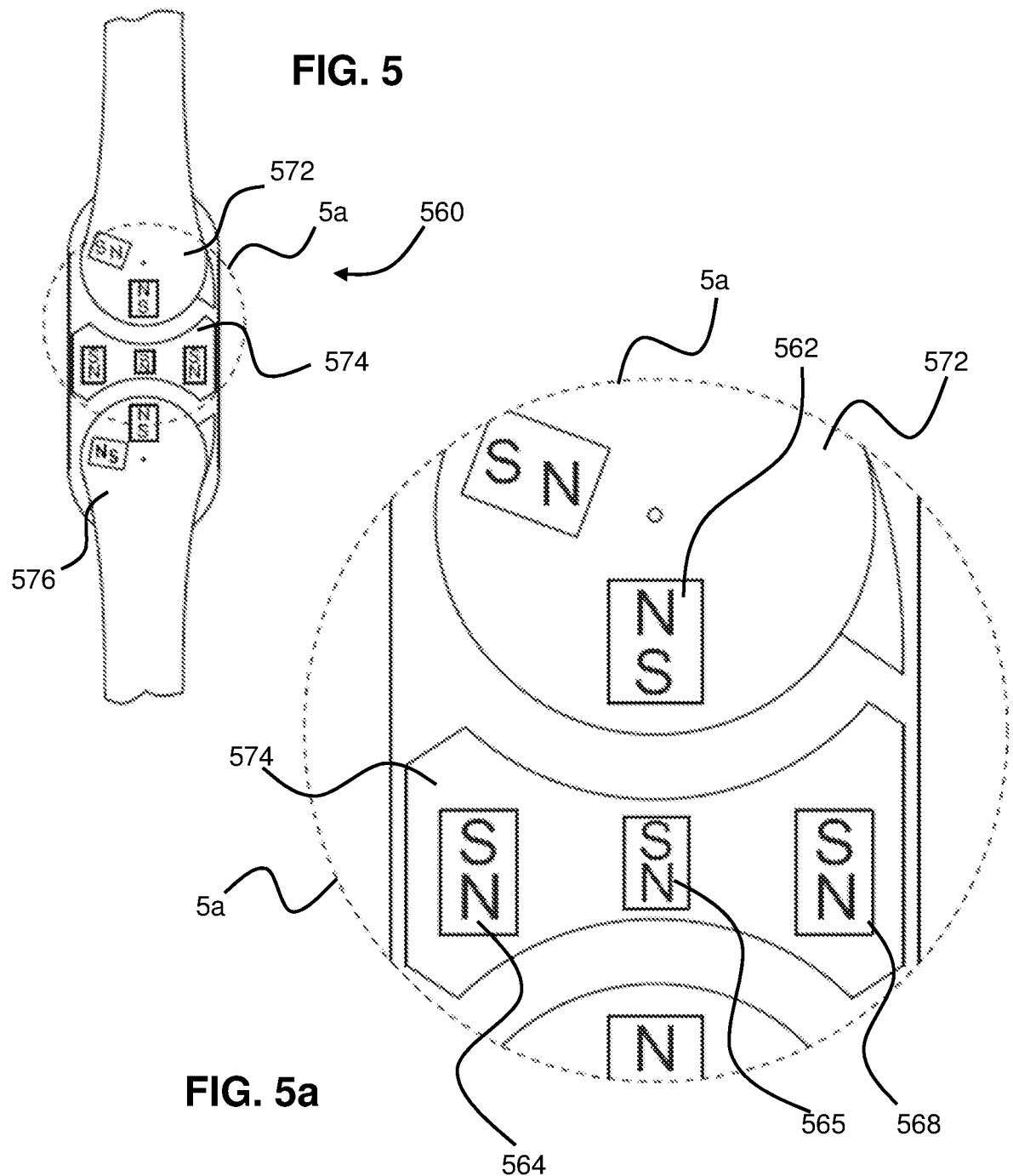

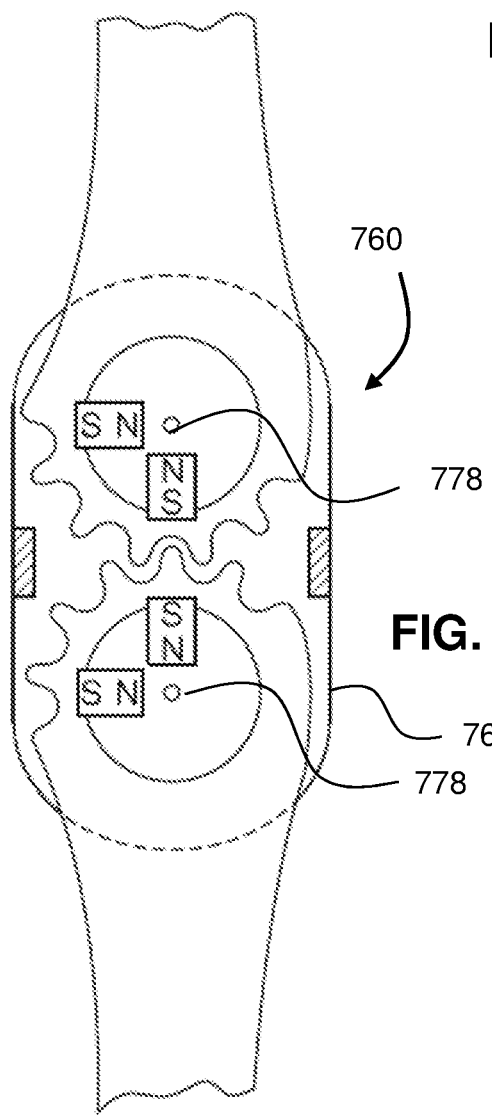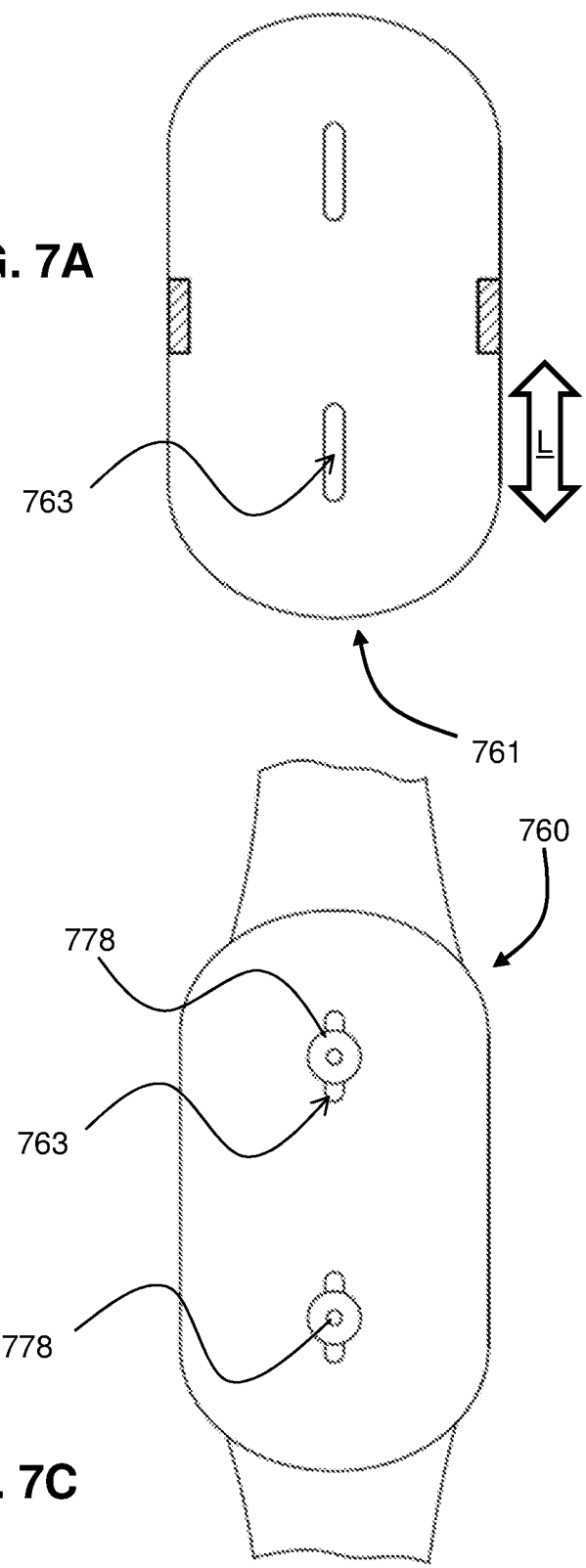

MAGNET ASSISTED ORTHOTIC BRACE

CROSS-REFERENCE TO RELATED APPLICATIONS

This application is a Continuation of U.S. patent application Ser. No. 14/604,982 filed on Jan. 26, 2015, entitled "MAGNET ASSISTED ORTHOTIC BRACE"; U.S. patent application Ser. No. 14/604,982 is a Continuation of U.S. patent application Ser. No. 12/781,212 filed on 17 May 2010, entitled "MAGNET ASSISTED ORTHOTIC BRACE", now U.S. Pat. No. 8,939,924; U.S. patent application Ser. No. 12/781,212 claims benefit to U.S. Patent Application No. 61/179,359 filed on 18 May 2009, entitled "MAGNET ASSISTED ORTHOTIC BRACE"; the entire content of each application referenced above is incorporated by reference in their entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable.

BACKGROUND OF THE INVENTION

Field of the Invention

Embodiments of the present invention relate to assisting orthotic braces in reducing or influencing the load on and between bone portions of a joint or shifting the weight bearing load on one compartment of the joint to another. Embodiments of the present invention relate to utilizing magnetic fields to influence orthotic braces and bone portions of a joint so as to help prevent pain, injury and/or allow healing of repaired cartilage, meniscus, repaired or reconstructed ligaments or fractured bone.

Background of the Invention

Regarding knee brace embodiments, presently available to practitioners are load-shifting braces which rely on pressure pads and straps that pull and/or push the femur and/or tibia in a direction that opens and unloads the affected compartment. Scientific clinical and laboratory studies have validated the performance of these brace types but reveals that their limitations are related to less effect in heavy patients (large legs); as the knee flexes for weight-bearing gate; and poor patient compliance because of the size and bulkiness of the braces.

Attempts to use magnets in braces or hinges have been made. For example, U.S. Pat. No. 7,150,721 to Guy M. Houser discloses a brace hinge having magnets used to sense hinge element positions. U.S. Pat. No. 6,517,503 to Jonathan M. Naft et al. discloses a brace having a hinge that locks the brace based on sensor signals to a magnetic coil that can trigger the brace to lock and unlock. However, neither of these embodiments provide a force on brace elements as is described herein.

Disclosures have been made regarding the use of magnets to address orthopedic problems directly in the bones of the joint. For example, U.S. Pat. No. 4,024,588 to Janssen, et al. describes artificial joints with magnets. U.S. Pat. No. 4,332,037 to Esformes et al. suggests an elbow joint including mechanically interlocking joint components with the inclusion of a magnetic force on the joint. U.S. Pat. No. 5,595,563 to Moisdon discloses a method of repositioning body parts through magnetic induction generated by extracorporeal magnetic or electromagnetic devices. U.S. Pat. No. 5,879,386 to Jore describes an apparatus to hold bones apart which can also be adjustable from inside the joint, possibly through arthroscopic means. U.S. Pat. Nos. 7,101,374 and 6,599,321 to Edward R. Hyde disclose the use of magnet arrays as direct implant in the bones of joints. However, these embodiments require invasive surgical procedures to implement.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented.

Conventional approaches to compartmental osteoarthritis and other joint maladies have included placing a brace on the limb surrounding the joint. Such braces aim to impart force or leverage on the joint in order to relieve compressive forces within a portion of the joint, or to reduce the load on that portion. It is well documented that the force shifting abilities of a brace that relies only on straps, preformed struts or pressure pads, function little to none after 20 degrees of flexion. With the combined use of magnetic repulsion forces, the load shifting capabilities of embodiments of the disclosed hinge and brace can function from full knee extension into full knee flexion and in both the weight bearing and non-weight bearing condition.

It is an object of one embodiment of the disclosed orthotic brace to combine load shifting capabilities of specialty bracing with the added force of magnetic repulsion through a portion or complete range of knee motion. Some embodiments of the specially designed brace and hinge can re-direct repulsion forces into one or more superior/inferior directions, thus distracting the joint surfaces on the side of the joint that the hinge/magnet system is applied. Some embodiments of the brace also provide the ability to influence the joint through greater degrees of flexion.

Some embodiments of the brace and hinge design are capable of reducing the force put on joint bones as well was influence the bones in pre-determined manner to bias the joint into certain positions or to vary the force in different points of joint flexion.

It is an object of an embodiment of the invention to provide an orthotic brace hinge having a first hinge element, a second hinge element, the first and second hinge elements being operably connected and the first and second hinge element have a first and second magnetic field respectively whereby the first and second magnetic fields provide a force urging the first and second hinge elements in a pre-determined direction. In some of these embodiments, the first and second magnetic fields oppose each other, the force urging the first and second hinge elements is a repelling force, the first and second hinge elements being operably connected about a hinge longitudinal axis and at least one of the hinge elements is movable generally parallel to the hinge longitudinal axis whereby the repelling force is capable of moving at least one of the hinge elements along the hinge longitudinal axis. In some of these embodiments, at least one of the hinge elements is movable about a pivot and the pre-determined direction is in a direction about the pivot. In some of these embodiments, the force is at least about 100 pounds. In some of these embodiments, the magnetic field is formed by a magnetic array. In some of these embodiments, the hinge is capable of moving into at least to a first flex position and a second flex position and the force at the first flex position is different than the force at the second flex position. In some of these embodiments, at least one of the magnetic fields is formed by a magnetic array and the magnetic fields urge the first and second hinge elements about the pivot according to a pre-determined magnetic field profile of the magnetic fields. In some of these embodiments, the first and second magnetic fields attract each other and the force urging the hinge elements in a pre-determined direction is an attracting force, the first and second hinge elements being operably connected and at least one of the hinge elements being movable generally parallel to a hinge longitudinal axis whereby the attracting force is capable of moving at least one of the hinge elements along the hinge longitudinal axis. In some of these embodiments, a third magnetic field is provided on one of the first and second hinge elements providing a repelling force to at least one of the first and second hinge elements further urging the first and second hinge elements in a pre-determined direction.

It is another object of an embodiment of the invention to provide an orthotic brace having a first and a second lever operably connected about a pivot and the first and second lever being urged in a pre-determined direction by a magnetic force from a magnetic field. In some of these embodiments, the pivot is formed by a pivot connection connecting the first and second lever, the magnetic field comprises a first and second magnetic field, the first and second magnetic field oppose each other causing the magnetic force to be a repelling force and the first magnetic field is connected to the first lever and the second magnetic field is connected to the second lever. In some of these embodiments, the pivot is formed by a pivot connection connecting the first and second lever, the magnetic field comprises a first and second magnetic field, the first and second magnetic field attract each other causing the magnetic force to be an attracting force; and the first magnetic field is connected to the first lever and the second magnetic field is connected to the second lever. In some of the embodiments, the pivot connection comprises at least one pivot connector pivotally connecting at least one of the first and second levers to a hinge base whereby the at least one lever is capable of pivoting relative to the other lever and the pivot connector also moveably connecting at least one of the first and second levers to the hinge base whereby the at least one lever is capable of moving along a longitudinal axis of the brace. In some of the embodiments, the pivot connection comprises at least one hinge operably connecting at least one of the first and second lever, the hinge comprising a pivot connector and at least one wheel, the pivot connector pivotally connected to the wheel and the wheel operatively connected to at least one of the levers whereby one lever can pivot relative to the other lever. In some of the embodiments, at least one of the first and second magnetic fields is provided by a magnetic array. In some of the embodiments, the first magnetic field is connected to at least one of the first and second lever and the second magnetic field is operably connected to a portion of the hinge such as a hinge base. In some of the embodiments of the orthotic brace, the first lever and the second lever have a longitudinal axis, the magnetic field is formed by at least one magnetic array and the repelling force urges movement of the first and second magnetic fields to resist an extension of the upper and lower brace lever.

It is yet another object of an embodiment of the invention to provide an orthotic brace for a joint of an animal's body, the brace comprising a first brace frame adapted for connection to a first portion of an animal's body on a first side of a joint, a second brace frame adapted for connection to a second portion of the animal's body on a second side of the joint, a pivot connection between the first and second brace frames adapted to be generally aligned with the joint when the brace is attached to the animal, a force element operably connected to at least one of the first and second brace frames imparting a force on one of the first and second brace frames in a pre-determined direction and the force comprising a magnetic field. In some of the embodiments, the pivot connection enables one of the first and second brace frames to pivot relative to the other brace frame and the pre-determined direction is about the pivot connection. In some of the embodiments, the force is a repelling force.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only illustrative embodiments of the invention and are not therefore to be considered to be limiting of its scope, the invention will be described and explained with additional specificity and detail through the use of the accompanying drawings in which:

FIG. 5 is a side view of one embodiment of an orthotic brace hinge assembly incorporating a magnet array and highlighting section 5a of the hinge;

FIG. 5a is a detailed view of section 5a of FIG. 5;

FIG. 7A illustrates a side view of one embodiment of a back plate of an orthotic brace hinge assembly prior to installing a magnet array;

FIG. 7B illustrates a side view of one embodiment of an orthotic brace hinge assembly incorporating a magnet array;

FIG. 7C illustrates a side view of an enclosed orthotic brace hinge assembly incorporating a magnet array;

DETAILED DESCRIPTION OF THE INVENTION

A magnet assisted orthotic brace system will now be described in detail with reference to the accompanying drawings. It will be appreciated that, while the following description focuses on an orthotic brace system that uses magnetic forces to reduce joint forces on a knee, the systems and methods disclosed herein have wide applicability. For example, the orthotic brace system described herein may be readily employed with other joints on a patient's body such as knee, finger, elbow, wrist or shoulder joints. Notwithstanding the specific example embodiments set forth below, all such variations and modifications that would be envisioned by one of ordinary skill in the art are intended to fall within the scope of this disclosure.

Some embodiments of the disclosed brace and hinge can require fewer straps and less prominent hinges by virtue of the size and placement of one or more magnets in a magnetic array. The magnets are placed so as to repel or attract each other as they come into proximity of each other through the motion of knee and brace components.

As is described below, multiple placements and configurations of magnet arrays are possible and contemplated to account for the different treatment or load shifting affects desired. For example, unlike present brace designs, as the upper and lower hinge elements get closer due to knee angle and increased weight, the magnets can be placed and configured to naturally increase force and repel themselves apart or urge them in pre-determined directions.

Additionally, multicentric configurations of brace hinge embodiments allows the brace components to distract in a controlled direction and because of the firm attachment of the brace components to the thigh and lower leg, the articular surfaces of the femur and tibia can be urged to separate due to magnetic repulsion of the contiguous magnets. As the knee rotates thru its range of motion from extension to flexion, a series of magnets in an array can continually repel each other and urge the joint in pre-determined directions.

Orthotic Brace in General:

A typical orthotic brace comprises generally a joint stabilizing bracing element and a plurality of attaching elements to bind the bracing element to the soft tissue of the limb elements, above and below a joint. An example of a popular joint brace is illustrated in U.S. Pat. No. 6,623,439, filed Aug. 31, 2001 to Kim Alex Nelson et al. entitled "Contoured Knee Brace Frame" which is herein incorporated by reference in its entirety.

Figure 1:
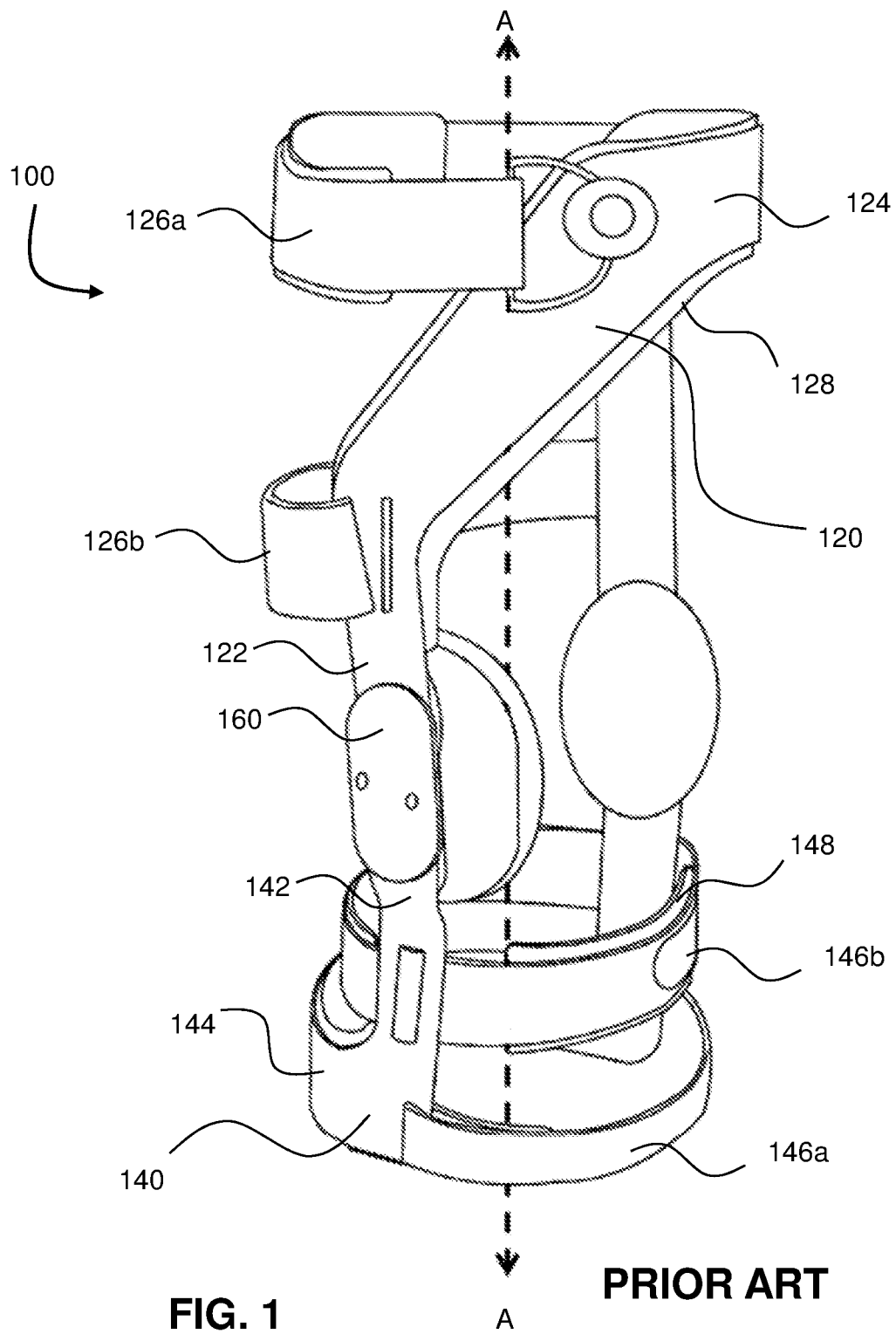
FIG. 1 illustrates a prior art configuration of a knee brace having a hinge.

FIG. 1 illustrates one embodiment of an orthotic brace system 100 for a knee. The bracing element comprises generally of a first and second frame operably connected by a pivot structure such as a hinge 160. For the embodiment shown, the orthotic brace system includes a femur frame, generally designated 120 and a tibia frame, generally designated, 140. The frames 120 and 140 are operatively connected at one or both sides of the leg proximate the knee by a pivot or hinge 160. In some embodiments, portions of the frames can be used as parts of the hinge structure. The hinge structure permits the distal end portions of the femoral frame 120 and the tibial frame 140 to be displaced relative to each other as the brace and joint is flexed. The brace has a general longitudinal axis as shown as dashed line A-A in FIG. 1. Generally parallel to this brace longitudinal axis is a hinge longitudinal axis. These longitudinal axis generally parallel the brace levers 122 and 142 when the joint, and therefore the brace, is extended. The brace levers have a lever longitudinal axis generally parallel to the brace and hinge longitudinal axis. The movement of the distal ends of the frame of an orthotic brace is substantially relative rotation in a plane, however, monocentric, bicentric, and polycentric hinges are utilized in orthotic braces and contemplated for embodiments here to more precisely conform the lever displacement to the often complex articulation of specific joints.

The femoral frame 120 comprises a generally elongated, usually flat, femoral side bar or lever 122 that extends generally longitudinally along the one or both sides of the thigh and one or more femoral side bar attaching portion 124. FIG. 1 illustrates one example of the lever 122 as being a portion of the femoral frame 120. Similarly, the tibial frame 140 comprises an elongated, usually flat, tibial side bar or lever 142 located generally longitudinally along the one or both sides of the calf and one or more tibial side bar attaching portions 144. As shown here, the frames of some braces for the knee, elbow, and other joints include pairs of hinged bars, generally arranged longitudinally along opposite sides of the limb, these being a lateral or outer side bar and a substantially similar medial or inner side bar on the inside of the limb.

One embodiment of a knee brace is attached to the limb elements, the femur above the knee, and the tibia below the knee, by a plurality of attaching elements that constrain the frames to the soft tissue of the limb elements. The femoral frame 120 is bound to the femur at its distal end by the femoral side bar attaching portion 124, such as an upper thigh cuff. The upper thigh cuff of the brace generally extends across the thigh and is operatively connected to an upper thigh binding 126a. Although not necessary, this embodiment shows the thigh cuff extending across the anterior of the thigh. The upper thigh binding is wrapped around the thigh and constrains the cuff and a portion of the femoral frame to the thigh. As shown in 1, multiple bindings 126a and 126b may be used to secure the frame to the thigh. In one brace embodiment, the bindings comprise a fabric binding wrapped around the leg and the outer side of the frame. A pad 128 may also be held in position by the binding to spread the load produced by the binding over a greater area of the soft tissue of the thigh.

Similarly, another attaching portion 144 forms a lower calf cuff that extends across the posterior or the anterior of the tibia. A lower calf cuff is constrained to the lower limb by one or more lower calf bindings 146a and 146b that extend across the tibia and are operatively connected to the calf cuff. The lower calf cuff may also have a pad 148 to spread the load produced by the binding over a greater area of the shin.

The upper thigh and calf cuffs can be made of any material such as metal, plastics or composites that are able to secure the brace to the limbs. Generally, the cuffs are substantially rigid and often formably adjustable to accommodate thighs and calfs of differing curvatures. A substantially rigid but formably adjustable cuff can be fashioned from a metal core, preferably of aluminum, laminated on both sides with a covering, typically plastic, to protect the wearer and others from sharp edges or corners and improve wearer comfort.

In some embodiments, the lower calf cuff comprises a flexible plastic, such as polyethylene. In embodiments, a flexible lower calf cuff base is desirable to accommodate a variety of calf girths and permit adjustment of the tibial side bar to prevent twisting relative to the hinge which might otherwise be caused by calves that are undersized or oversized for the lower calf cuff base.

Hinge Assembly and Hinge Magnet Array:

Embodiments of the present invention generally utilize magnetic forces to urge brace elements in a pre-determined direction so the brace can be used to stabilize and/or maintain adjacent joint portion in pre-determined desired relationships and for constraining motion and/or rotation of the joint portions. These forces are able to improve the characteristics of an orthotic brace. Biomechanically this assistance is helpful because the force on a person's knee is significant. The force on a knee can be about three times a patient's body weight when they are walking. When other activities are undertaken, the forces can reach six to ten times body weight. That is, the force on a 200-pound person's knees while walking is 600 pounds, and when they are climbing, running, squatting, etc. the force approaches 1200-2000 pounds.

Figure 2A:
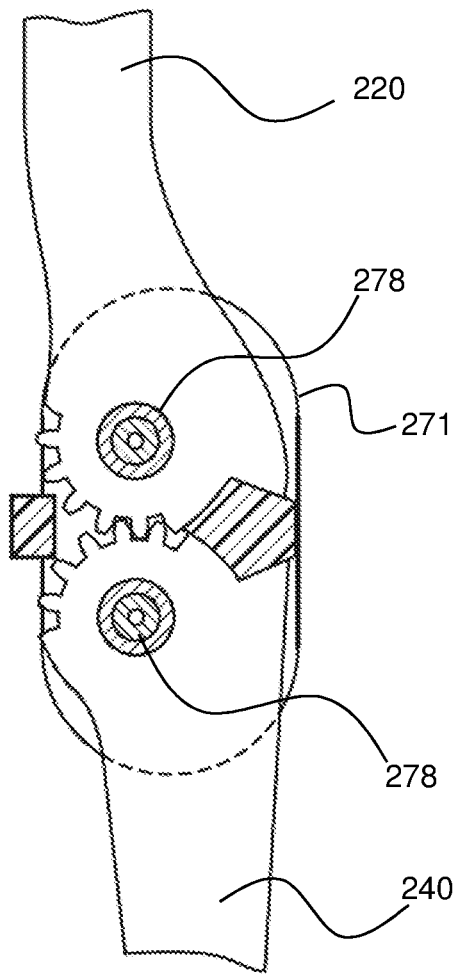
FIG. 2A illustrates a configuration of a knee brace hinge.

One example of a hinge assembly as used in orthotic braces is shown in FIG. 2A. To shift and influence loads applied to the knee, this embodiment relies on the direct mechanical contact of frame elements 220 and 240 and the frictional engagement of frame elements (the cuffs) to the patients body. As shown the lever portions of the frame elements 220 and 240 are operatively connected by pivot connectors and a hinge base 271 to form a hinge that can pivot about the pivots 278. The pivots can be any type of operational connection that allows at least one of the hinge elements to pivot in relation to the other element. Suitable connections include those made by connectors such as, but not limited to rivets, screws, rods or nuts and bolts received through slots in the brace elements. Connections with ball bearings and the like are also contemplated. Here, pivot connectors such as rivets are shown.

Embodiments of the present invention recognize that magnets and magnetic fields can be force elements that provide additional forces on elements of the orthotic brace through the hinge elements or other operably connected brace elements. By using the repelling and attracting forces of magnets, the mechanical contact can be replaced or supplemented to reduce the force put on joint bones as well was influence the bones in a pre-determined manner to bias and urge the joint into certain positions or to vary the force in different points of joint flexion.

Figure 2B:
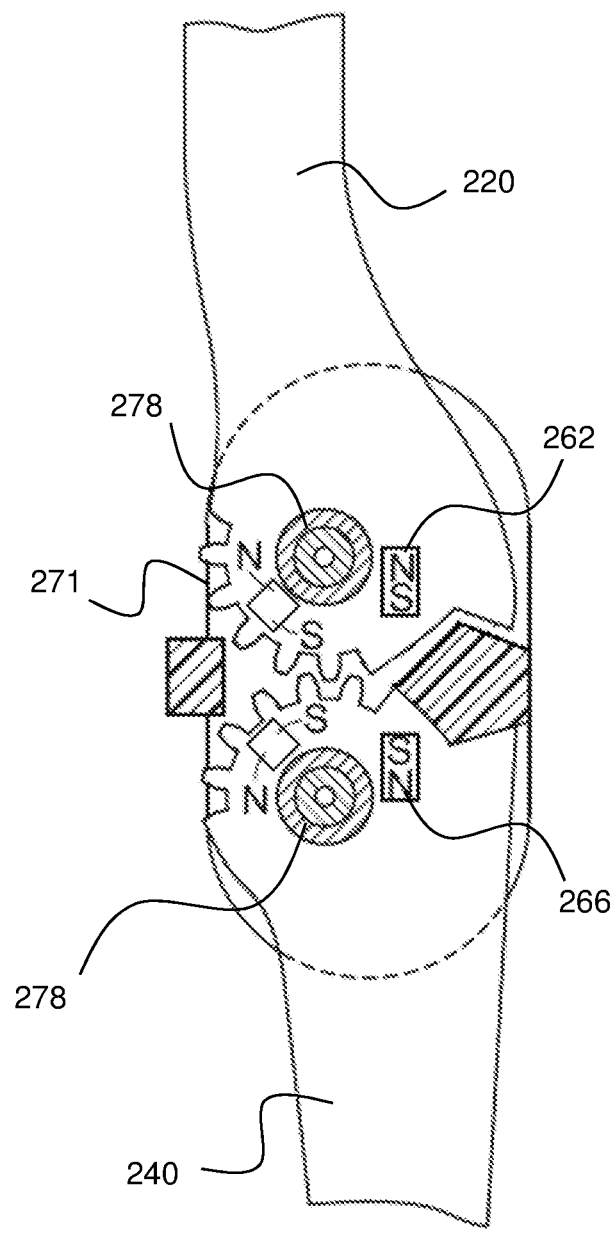
FIG. 2B illustrates one embodiment of a knee brace hinge with magnets attached to hinge elements.

The embodiment shown in FIG. 2B, using a structure similar to that of FIG. 2A, provides a magnetic field added to the proximal ends of the brace elements, or the levers, to provide a repelling force. As shown in this and other figures, N reflects a "North" pole and S reflects another, or "South" pole. The magnetic fields can be added by connecting one or more magnets to the brace elements. If they are connected, the connection can be directly to the brace elements or to hinge elements through any connection means such as but not limited to adhesives, screws, clips, hooks or recesses in the elements. In this embodiment, the proximal ends of the brace elements function as hinge elements which are operably connected to each other by a hinge base 271 with connectors that function as pivots 278. In this embodiment, there is also some freedom in the levers to move through the hinge along a longitudinal axis. At least one of the pivot connections is able to move along a longitudinal axis of the hinge that corresponds generally with the knee joint when extended. With this configuration, as the opposing poles of magnets 262 and 266 are positioned next to each, the repelling force of the magnetic fields provide an additional force against the levers. Since the levers are able to move longitudinally, the force can be translated to the lever through that longitudinal movement and on to other elements of the frame elements 220 and 240. When those frame elements are attached to the limbs of the patient, the repelling force can then be translated to the limbs around the joint.

Although the embodiments shown in FIG. 2B shows the magnets located in certain locations on the hinge elements, it is understood that the magnet fields can be placed anywhere on the elements to provide the desired effect, including on the gear teeth themselves, on the base of the hinge or on a hinge insert as discussed below. The magnetic fields can also be added by manufacturing hinge elements to include magnetic material or otherwise integrate magnetic materials.

Figure 3A:
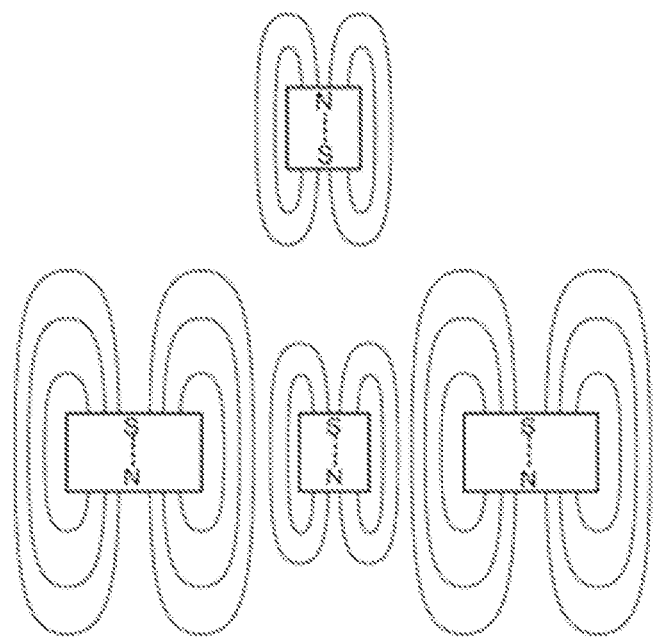
FIG. 3A illustrates the magnetic flux lines associated with one embodiment of an array of magnets.

The use of magnetic fields can be enhanced by using magnet arrays. The use of magnet arrays as implants directly in bones, is described in U.S. Pat. No. 7,101,374 to Edward R. Hyde filed May 13, 2002 entitled "Magnetic Array Implant" and U.S. Pat. No. 6,599,321 to Edward R. Hyde filed May 4, 2001 entitled "Magnetic Array Implant and Prosthesis" (collectively HYDE) both of which are herein incorporated by reference in their entirety. Embodiments of the present invention utilize some of the magnetic field properties of arrays as described in HYDE as well as some of the techniques in configuring the fields. FIG. 3A, shows the magnetic flux lines of a composite magnetic field generated by the magnet array shown. Similar to the techniques described in HYDE, these magnetic flux lines may be used to assess a spatial distribution pattern of magnetic intensity of the composite magnetic filed of the magnet array. For example, the magnetic intensity can be assessed in terms of "magnetic flux" which is defined as the amount of magnetic flux lines crossing a given area. Alternatively, the magnetic flux may be calculated as an integral of a component of magnetic flux density perpendicular to the area divided by the area. Comparison of the magnetic flux densities reveals that the magnetic intensity or magnetic flux decreases as the distance between magnets increases. Additionally, as shown, magnetic flux lines emanating from stronger outer magnets extend farther than flux lines emanating from the weaker central magnet.

Figure 3B:
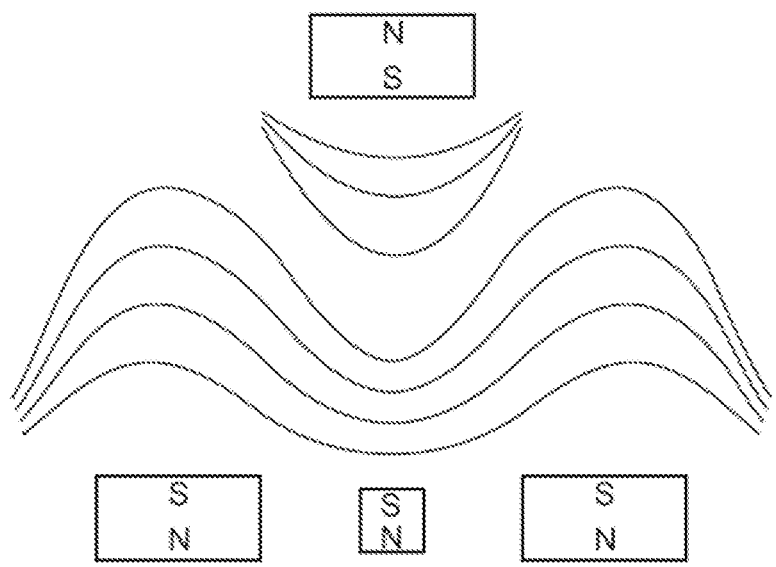
FIG. 3B illustrates the magnet array equipotential lines associated with one embodiment of an array of magnets.

The spatial distribution pattern of the magnetic intensity (or flux) can also be assessed by mapping equipotential lines of force for the composite magnetic field. FIG. 3B is an example of a cross-sectional schematic view of equipotential lines of the composite magnetic field generated around the magnetic array of FIG. 3A. The equipotential lines are curvilinear lines representing a vector sum of individual magnetic fields generated by center and peripheral magnets. The mapping of equipotential lines can facilitate the analysis of composite magnetic fields as well as provides a graphic representation of the characteristics of the composite magnetic fields. The map of equipotential lines in FIG. 3B demonstrates that the contour of the equipotential lines depends not only on the specific characteristics of the magnets (i.e., strength, material composition, size, shape, cross-sectional area, position, and orientation) but also on the distance from the magnet(s).

Figure 4A:
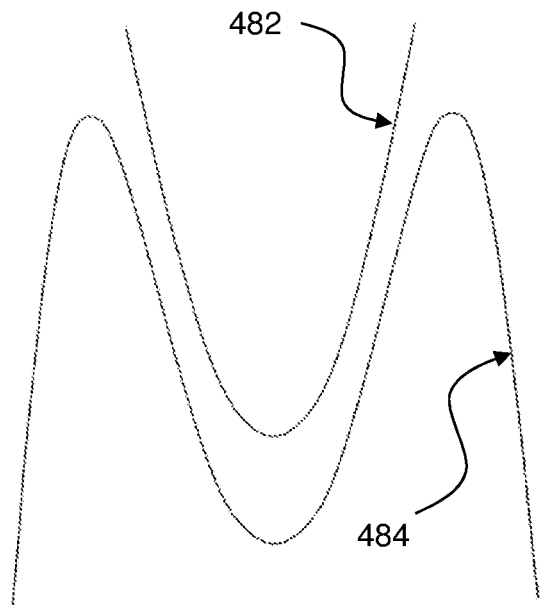
FIGS. 4A and 4B illustrates equipotential lines associated with multiple embodiments of magnet arrays showing the potential variations of forces according to magnet array configurations.
Figure 4B:
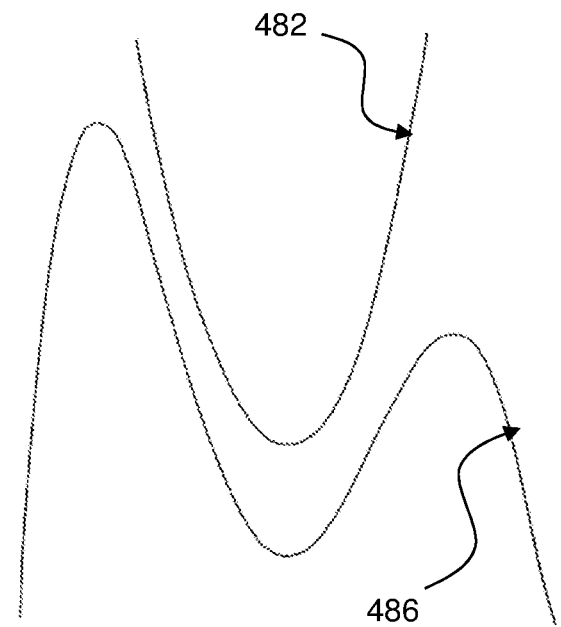

FIGS. 4A and 4B illustrate examples of two different equipotential line configurations possible with the use of different magnetic fields from different magnetic arrays. As is shown, the force required to move the upper field 482 to the right through lower field represented by equipotential line 484 in FIG. 4A should be less than the force required to move the upper field represented by equipotential line 482 to the right through lower field represented by equipotential line 486 in FIG. 4B. This example illustrates how magnetic fields can be configured to provide pre-determined magnetic field profiles to urge magnetic field, magnets and elements attached to the magnets, in a pre-determined direction.

In general, magnets and magnetic arrays according to embodiments of the present invention are made of permanent magnets. Examples of such permanent magnets preferably include, but not limited to, rare earth cobalt magnets (e.g., samarium-cobalt, SmCo), neodymium, ceramic, alnico and rare earth iron boron magnets (e.g., sintered neodymium-iron-boron, NdFeB). Magnetic arrays according to the invention may further include diamagnetic, paramagnetic, ferromagnetic, anti-ferromagnetic, and/or ferromagnetic material, and/or any other materials that may be incorporated to affect or vary the configuration of the composite magnetic field created around the magnetic arrays. Steel or other ferromagnetic material may be used to complete a circuit by contacting the magnets on their back surfaces.

The magnetic field properties are different depending on factors such as the strength of the magnet and the distance of the field from the magnet. Recognizing the ability to vary the magnetic application of magnet fields, different configurations of magnet arrays can be used to create different force profiles. The force profiles can be helpful to help influence movement in a particular direction, to limit the extension or hyperextension of a joint or they can be helpful in providing force relief from specific points of joint flexion, or specific compartments of the joint that may benefit from the force relief such as the point of arthritis in the joint.

The force profile resulting from the interaction of the magnet fields also changes as the hinge and magnets move through different positions. As the brace is put into flexion, this movement through different positions can provide for one force to be applied when the hinge is in one first position and another second force to be applied when the hinge is in another second position, or any of n positions.

The design of magnetic fields can be accomplished using the methods and tools similar to those described in HYDE. The composite magnetic field of a magnetic array may be quantitatively assessed utilizing the governing equations (e.g., differential equations of divergence and curl of a magnetic flux density vector) of magnetostatics or magnetodynamics, with appropriate boundary conditions and delineated properties of the conducting medium. The composite magnetic field of a complicated magnetic array may also be analytically estimated by approximating the terms of the governing equations and/or the boundary conditions. Alternatively, such solutions and/or estimations may also be obtained by numerical methods such as finite element; finite difference or boundary element analysis or by computer simulation using software which is commercially available, for example, INTEGRATED CAE from Integrated Engineering Software, Winnipig, Manatoba, Canada and Advanced Magnetic Field Design Suite from Field Precision of Albuquerque, N. Mex., USA. The magnetic arrays, and/or the magnetic apparatus may also be deduced from the pre-determined distribution pattern of magnetic flux lines and/or equipotential lines of composite magnetic fields. In theory, the preferred configuration of the magnets and magnetic array can be obtained by finding the solution of the governing equations of magnetostatics or magnetodynamics with the desired pre-determined composite magnetic fields as the boundary conditions.

The force profile that can be provided by the force elements and the brace can be of any magnitude, whether attracting or repelling. In some embodiments, the force profile of the magnetic field is designed to provide relief for the wearer when standing at rest. For that case, the force profile may only need to provide a repelling force of about 100 or 150 or 300 pounds depending on the wearer. In other embodiments, the force profile of the magnetic field is designed to accommodate a wearer in different physical activities such as walking, playing soccer or running. Thereof the force profile that must be provided may get as high as a 1500 or 2000 or 2500 pound or even higher force.

The design of the magnetic field may also include Halbach arrays. The use of a Halbach array is beneficial in that is can enhance the strength of the magnetic field in one direction while significantly reducing strength of the field in the other direction.

Figure 6:
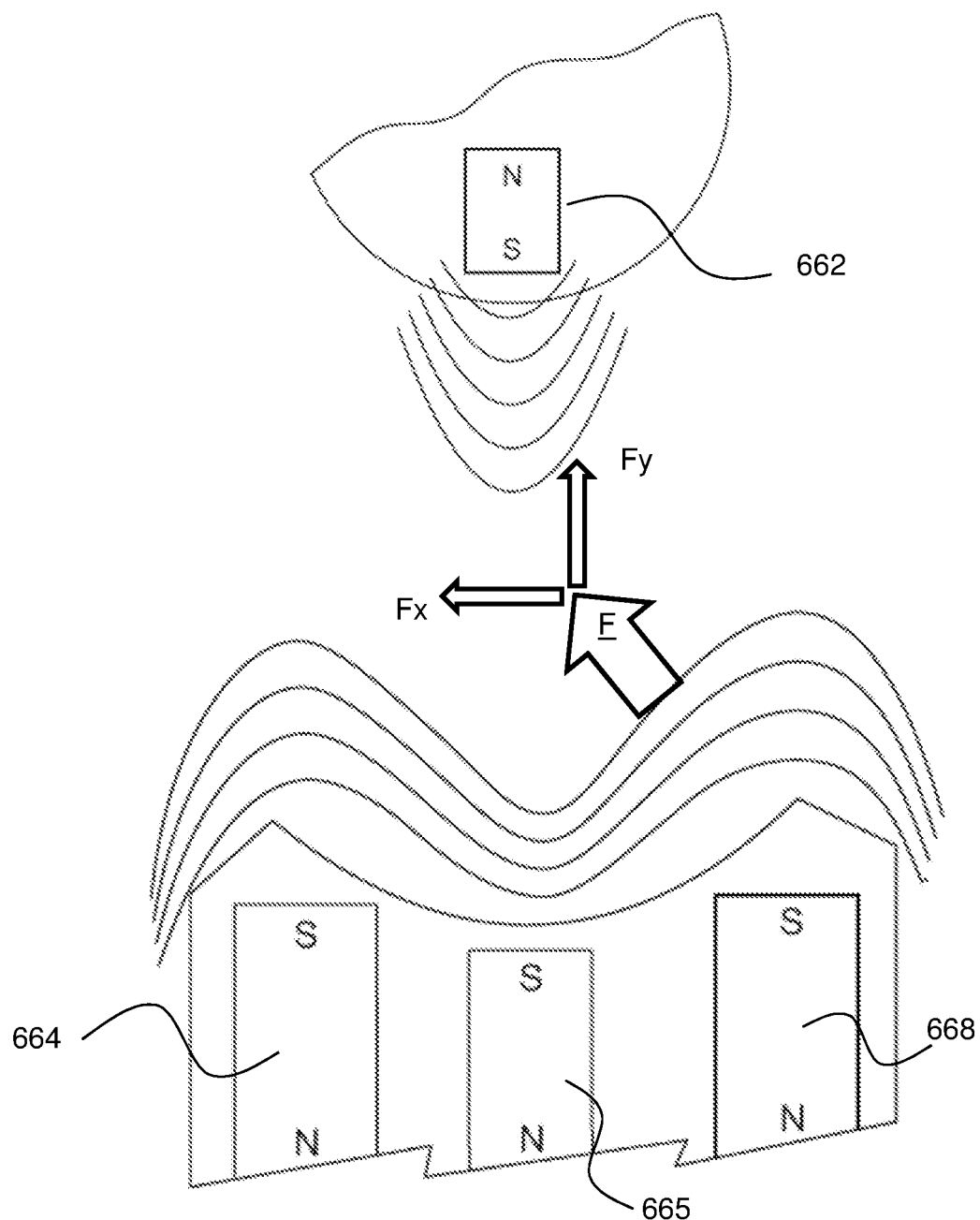
FIG. 6 illustrates equipotential lines associated with one embodiment of an orthotic brace hinge incorporating a magnet array.

As shown in the embodiments of FIGS. 5, 5a and 6, a magnetic array can be used to provide a force profile in a hinge assembly that is different at different positions of flex. FIG. 5 illustrates a hinge assembly 560 has an upper wheel 572 and a lower wheel 576 that rotate about their center. These wheels function as the upper and lower hinge elements and are each connected to the thigh and the tibial frame of the orthotic brace. These wheels allow the frames to pivot and rotate about the hinge assembly. In this embodiment, the wheels outer circumference rotates alongside insert 574. As the brace is put into flexion, the changes resulting from the wheel movement can provide for one force profile to be applied when the hinge is in one flex position and another force profile to be applied when the hinge is in a second flex position.

FIG. 5a shows an exploded view of section 5a of FIG. 5. With this example embodiment the magnetic fields of the wheel magnet 562 and insert magnets 564 and 568 are stronger magnets than insert magnet 565. The positioning of similar magnetic polls opposite each other on the hinge assembly wheels causes the magnetic fields to repel each other. The positioning of the weaker insert magnet 565 in between 568 and 564 causes a "valley" of a magnetic field or magnetic flux. When wheel magnet 562 is positioned opposite 565 as shown in FIG. 5, the field of 562 is urged away from the fields of 568 and 564 into this valley as shown in FIG. 6. When this magnet configuration is used on the hinge assembly, the hinge wheel is biased into a position where the field of wheel magnet 562 (and therefore the magnet and wheel) is biased in the position shown. By positioning the wheel magnets and the insert magnets as desired, forces can be placed on brace elements to move them in pre-determined directions as desired.

Illustrated in FIG. 6 is the possible multi-dimensional force that can be applied by some embodiments of hinges with magnetic fields and field arrays. As shown, the force from the magnetic field of 664, 665 and 668, represented as F, can translate into forces in multiple directions as shown here at Fx and Fy. As illustrated, the fields Fx and Fy as reacting to the fields caused by the field from magnet 662, can be designed to urge the source of the fields, and the attached hinge elements, in pre-determined directions. This urging can help separate brace elements and urge them in another direction causing elements to encourage or resist pivoting.

FIGS. 7A-7C show another embodiment of a hinge assembly 760 where a hinge insert is not used, but the magnets are positioned on the hinge wheels to give the same force effect. The hinge wheels can be separate elements to attach to the brace levers or the hinge wheels can be the ends of the levers similar to the embodiments shown here and in FIG. 2B. Similar to the embodiments shown in FIGS. 5 and 6, the magnets can be configured to provide the desired force affects on the hinge and the patient's joint.

FIG. 7A shows the hinge base 761 of one embodiment of a hinge assembly that provides for movement of the wheels allowing the force of the magnets to be translated to the wheel and the patient's limb. Some of this movement is provided by a movable connection that will allow movement generally parallel to the longitudinal axis of the brace and the hinge as shown by the arrow L of FIG. 7A. One embodiment of the moveable connection is at least one connector slot 763 in the hinge base that is sized to allow a pivot connector to be received and retained in the slot. FIG. 7B illustrates the hinge elements, which are the proximal ends of the brace elements, connected to the hinge base 761 of the hinge by a pivot connection such as with the pivot connectors 778. The connection can be any type of connection that will retain the hinge elements in place and allow them to pivot. Suitable connections include those made by connectors such as, but not limited to rivets, screws, rods or nuts and bolts received through slots in the brace elements. FIG. 7C illustrates the hinge elements with the front side of the hinge installed and showing the exposed pivot connectors 778. To provide the movable connection that allows movement of the hinge elements, the front side of the hinge also has at least one connector slot 763.

Although not required, as shown in FIGS. 7B, 2A and 2B, the use of meshed protrusions, like gear teeth, illustrate an example of one method of keeping the magnetic fields of one brace element in a known relationship to other elements and other magnetic fields as the hinge elements pivot. Although a consistent relationship is not required, the embodiment shown enables the magnetic field profiles to be designed so that the brace elements can be urged in pre-determined directions throughout flexion of the brace and joint wearing the brace.

Figure 8:
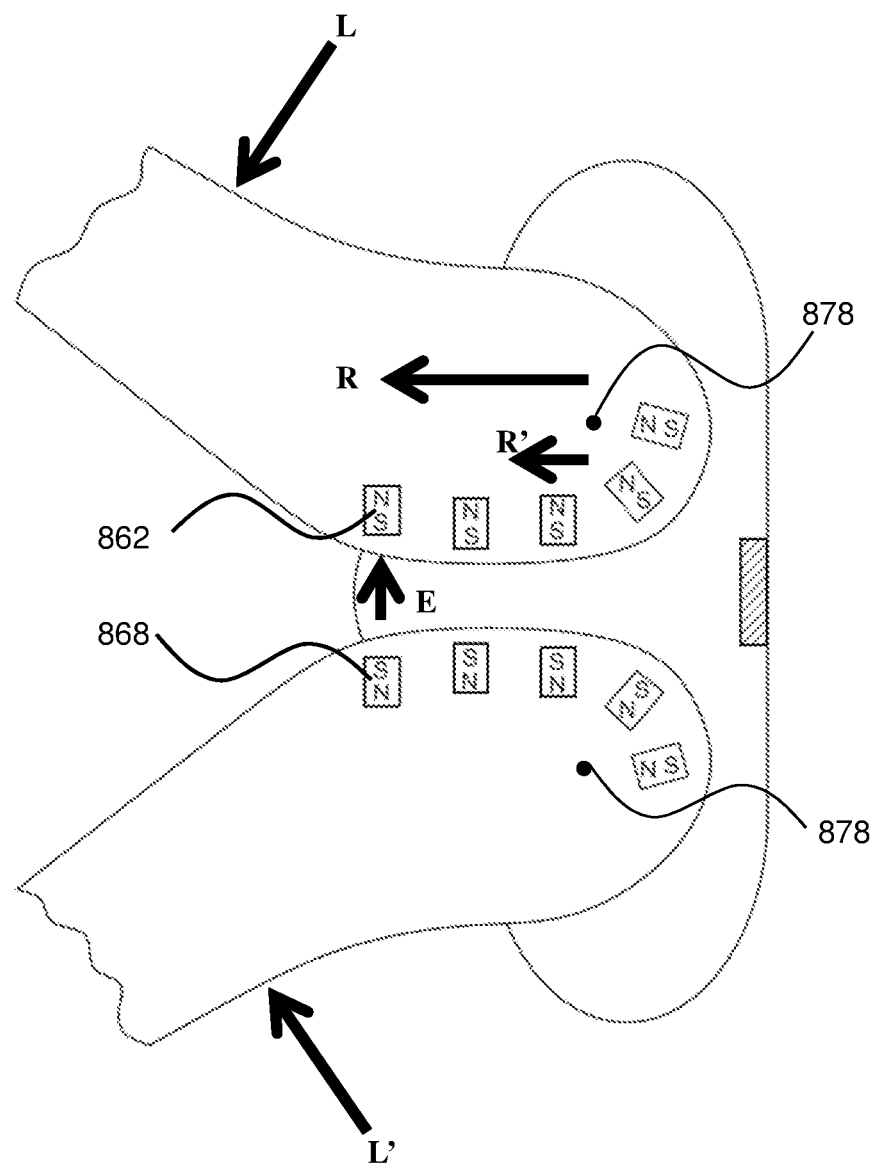
FIG. 8 illustrates an embodiment of the hinge assembly in one point of flexion.

The embodiment in FIG. 8 illustrates aspects of some embodiments of the present brace assembly. As shown, by having an extended surface available on the wheels or hinge elements, there is a force benefit gained by having the magnet force being further away from the pivot connection or the fulcrum. Using mathematical concepts similar to third class levers, by placing the magnets (e.g., 862 and 868) and magnetic force E a distance R from the pivot 878, the magnetic force E provides more of a resistance to the limb loads L and L' than would the same magnets being placed at a distance closer (R') to the pivot 878. As shown, when the brace is in flexion, magnets are put in close proximity along the extended surface. The extended surface can be configured based on common mathematical concepts such as logarithmic spirals, ellipses or other shapes that maintain the proximity of the magnets along the extended surface.

The force applied by the hinge assembly can be customized for each use and each patient. For a hinge to be used in a knee brace intended to reduce the force applied to the knees, the brace should provide a resistance force in extension greater than the weight applied to the joint. The brace can also accommodate the additional force caused by the act of using the joint as when a patient walks. Embodiments of the hinge can provide any resistance force profile depending on the magnet design and the needs of the patient. For example only, and not for limitation, one embodiment for a patient may have a force profile in flexion of at least about 100 pounds of resistance force and up to about 2500 pounds. It is also understood that for some positions of flexion of the hinge, it is possible for the force profile to create a state of attraction to assist the wearer.

Figure 9:
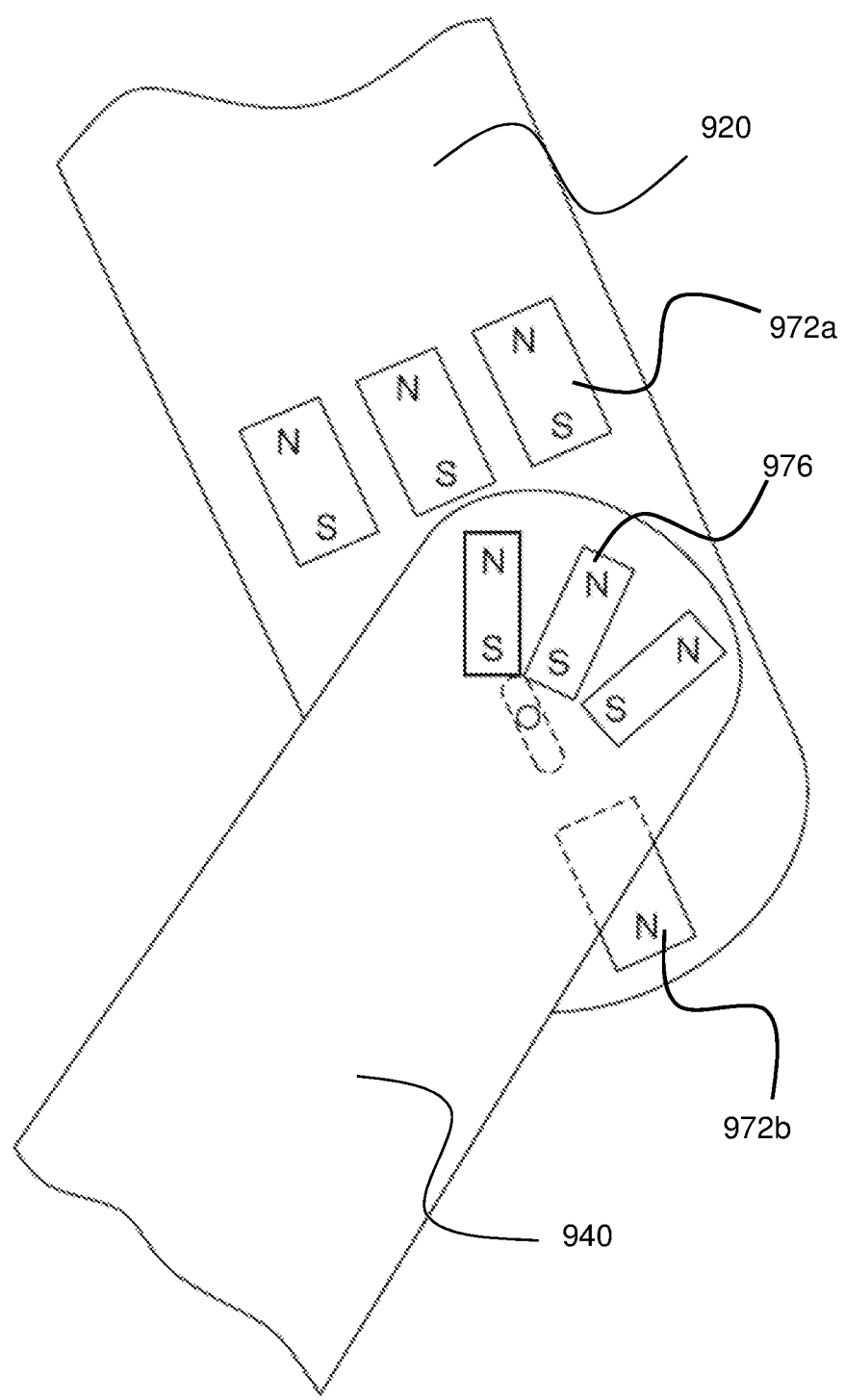
FIG. 9 illustrates one embodiment of a hinge having a magnet configuration including attractive forces.

Another embodiment of a hinge having magnets is shown in FIG. 9. FIG. 9 illustrates an embodiment that uses both the repelling force of magnetic fields as well as the attracting forces of the field to benefit the brace. As shown, the hinge wheels overlap so that it is possible to have one set of magnetic fields (from 976 and 972b) use a repelling force while another set of magnetic fields (from 972a and 976) uses an attracting force to influence the hinge elements to urge the lever and brace elements apart. This embodiment potentially allows a greater force to be applied with the use of fewer magnets. This feature can be used to reduce the size of brace elements, increase the force applied by the brace or both.

It is understood that in embodiments similar to FIG. 9, the use of the attracting force of magnets can also be used to provide a singular force to benefit the brace. For example, if FIG. 9 did not have the lower magnet on the upper lever, the attractive forces would still urge the levers (e.g., 940 and 920) to reduce the force on a joint if the brace was worn.

In embodiments, the pivot connector for the wheels may also be supported by springs or other resilient materials that further help urge the wheels in a pre-determined direction.

Embodiments Having Magnetic Fields in Other Brace Elements:

It is also contemplated that magnets may be placed on other brace assembly elements to also give the desired force affect. One example of this is placing repelling magnets in series along the femur and tibial frame so that they can combine their forces to create a greater repelling force on the thigh and shin. The magnetic fields can also be added to other brace elements to interact with the hinge elements or levers. In embodiments, the frame will be generally be able to expand up and down the leg to translate the magnetic force, but bending about the knee will generally be done by the hinge.

Figure 10:
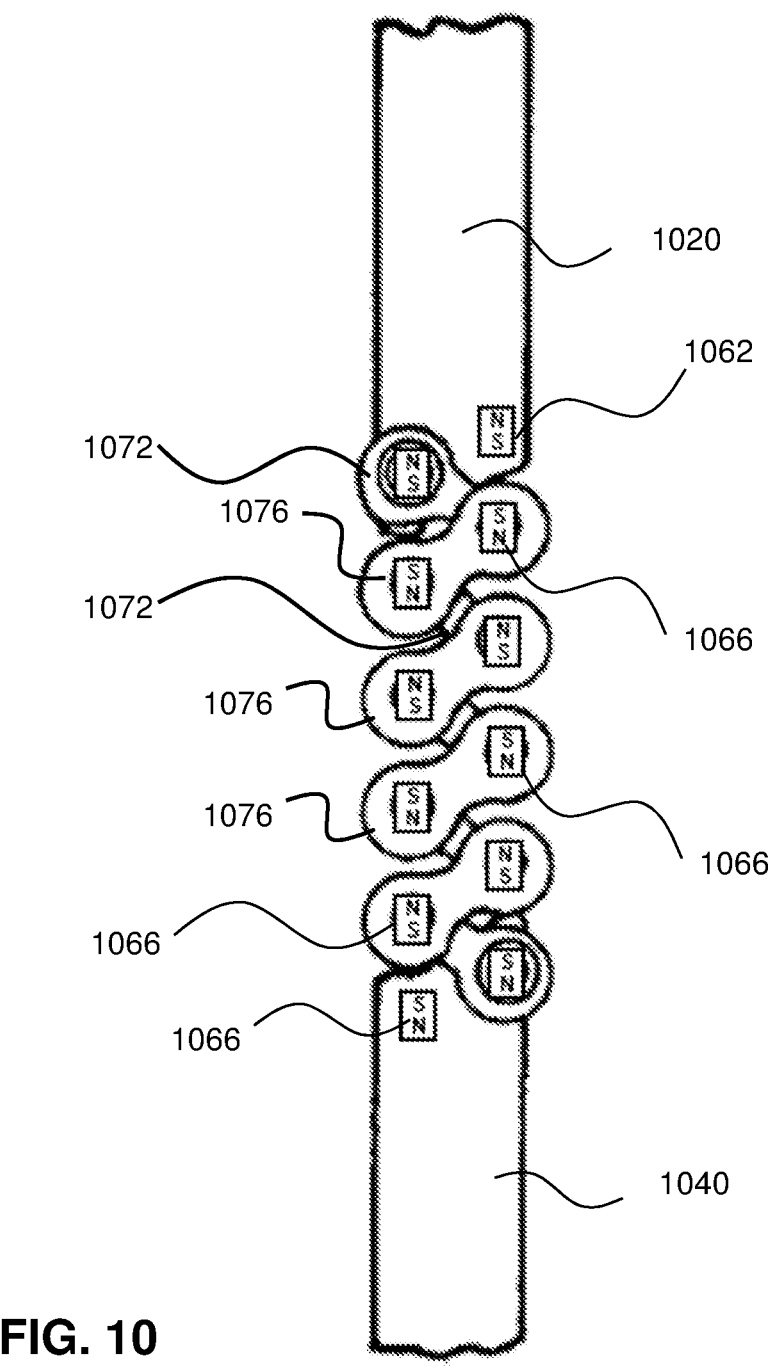
FIG. 10 illustrates one embodiment of a modified hinge frame portion or a poly-centric hinge incorporating magnets.

It is also contemplated that the magnets can be placed on multiple hinge elements such as in a polycentric hinge or in other pivot connections on frame elements to influence the movement of the brace elements. For example and not for limitation, the polycentric hinge embodiment disclosed in U.S. Pat. No. 4,393,542 to Gonzalo Martinez, filed Jul. 21, 1980 and entitled POLYCENTRIC HINGE FOR CASTBRACES, which herein incorporated by reference in its entirety, can have a magnetic field added to the hinge elements, or the links in Martinez, to influence the movement of the hinge elements. One example of an embodiment is shown in FIG. 10. As shown, several links, similar to those of a chain are interconnected to provide a bendable structure that individually or together can function as a hinge strut a hinge or a component of both or either element. As shown, some links function as upper hinge elements 1072 and others function as a lower hinge element 1076. On or integrated into the links are magnets such as 1062 and 1066 that provide a magnetic field urging the brace elements, such as the upper frame 1020 and the lower frame 1040 in a pre-determined direction. This direction can be used to provide joint distraction and or contraction to a patient wearing a brace with these elements. In the embodiment shown, the magnetic fields generally provide a repelling force. These types of embodiments can be used alone to function as the pivot connection or they can be integrated with any of the other embodiments disclosed such as, but not limited to, incorporating the features of FIG. 10 into the brace lever while also having hinge structures that provide additional control of the brace through magnet arrays connected to the hinge elements.

Embodiments with Interchangeable Magnet Arrays:

In some embodiments, the magnet arrays can be changed to provide varying forces. This may be desired when a single brace assembly or hinge design is made but it is helpful to provide different force patterns in the brace as may be provide by different magnet array configurations. For example, during the healing process from joint surgery, varying the resistance and load properties of the brace can help the healing and rehabilitation process. By having interchangeable magnet arrays, it is possible to vary the magnetic properties of the brace without having to exchange the entire brace. It is also helpful to provide different magnet array configurations for patients that have different forces on their joints due to weight or other factors.

Some embodiments of an interchangeable magnet array may be provided by having different magnet arrays that are preinstalled on a hinge insert such as insert 574 in FIG. 5. Through the use of clips, screws or other attaching means, the hinge insert can be changed to give the force properties desired. The magnets can also be added to and taken off of the hinge insert.

Some embodiments of an interchangeable magnet array may be provided by having removable magnets on the hinge wheels. For example, for the wheels of FIG. 7, interchangeable magnets or magnet arrays may be added to and taken off of the wheels to give the desired force properties. It is also understood that a wheel insert with magnets and magnet arrays could be attached to the wheels.

It is also contemplated that kits may be configured to include a pre-defined set of magnet arrays that correspond to the force properties expected to be needed. For example, during the rehabilitation of a patient from knee surgery, a series of interchangeable magnet arrays may be provided that provide more force repulsion immediately after the surgery while sets of provided array's can be interchanged to change the force profile as the joint heals.

Any combination of means to readily change the magnet arrays is contemplated.

Figure 11:
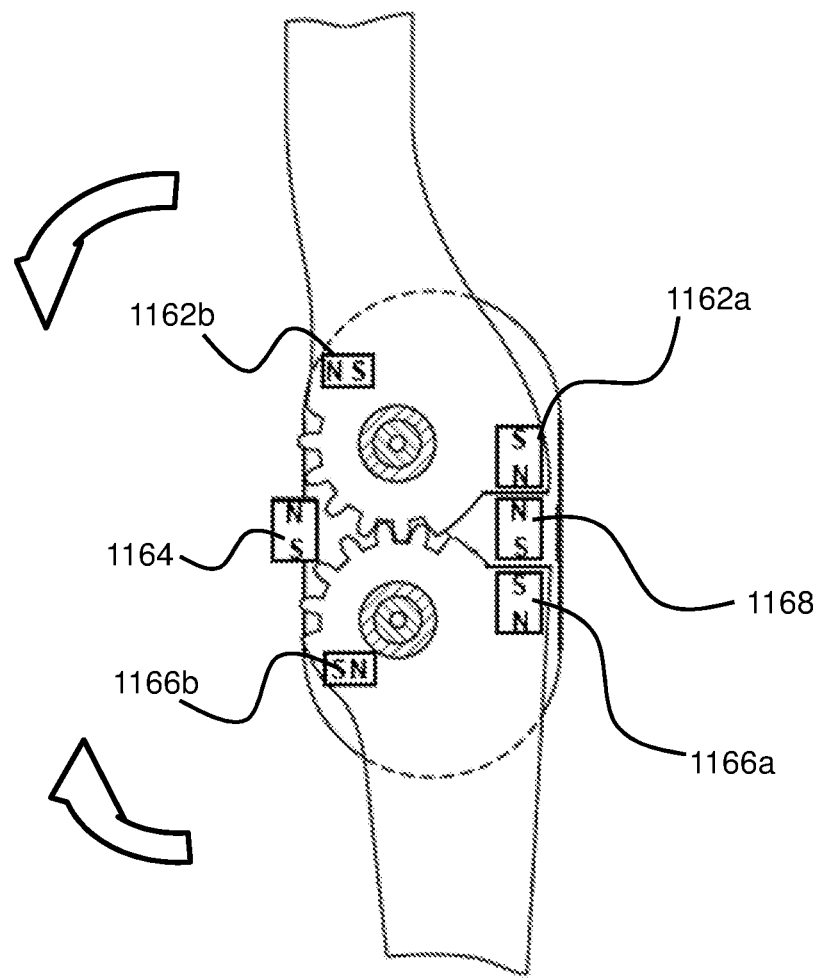
FIG. 11 illustrates one embodiment of a hinge with limited control of the brace.

Embodiments with Limited Control:

In some embodiments, the brace may also be designed to provide limited control such as focusing on limiting control of terminal flexion or extension or both in a joint. Referring to FIG. 11 is one embodiment where the hinges are primarily designed to limit the extension of the brace and the joint by the repelling forces of magnets 1162*a* and 1168 as well as magnet 1166*a* and 1168. Similarly, when the brace is put into flexion and the brace lever pivot, the magnets 1162*b*, 1164 and 1166*b* are brought into close proximity and the repelling forces of these magnets react to limit flexion of the brace and the joint. As described above, the hinges in these embodiments may be designed similar to any type of common hinge design, to include free or poly-centric hinges used alone or in combination with other configurations of magnets and brace elements.

Embodiments with Dynamically Adjusted Magnets or Materials:

In embodiments, the brace may also include a plurality of sensing and loading transducers to sense bracing parameters and alter one or more characteristics of the brace. In these embodiments, the brace can include sensing transducers to measure forces exerted by the attaching elements, including upper and lower cuffs and upper and lower tensioning structures; the angular displacement of the upper and lower frames of the brace, and stress in and displacement of the frames.

These embodiments can also include adjusting the magnet array properties dynamically to optimize the attachment of the brace to the joint, optimize the shape of the bracing element, and vary the resistance or assistance to joint articulation in response to changes in the limb or events affecting the limb or to accomplish a particular function or treatment regimen. By providing different electric currents, magnetic field in electromagnets may be varied. Additionally, dynamic magnetic materials can include but are not limited to electroactive polymers, piezoelectric compounds or a combination thereof.

The sensing and loading transducers can apply electrical charges to alter the magnetic properties of the magnet array or material. As a result, the brace system can dynamically alter the characteristics of the brace to respond to changes in the soft tissue supporting the brace, alter compartmental joint loading, and vary the resistance to joint flexion and extension as a function of, at least, a predefined treatment regimen, joint position, soft tissue conditions, and limb shape. There are a number of other known transducers that can be used to perform the various functions.

In some embodiments, the dynamic alteration of the magnetic properties of the brace and provide varied force repulsion at different angular displacements of the brace frames.

With respect to the above description then, it is to be realized that the optimum relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Although this invention has been described in the above forms with a certain degree of particularity, it is understood that the present disclosure has been made only by way of example and numerous changes in the details of construction and combination and arrangement of parts may be resorted to without departing from the spirit and scope of the invention.

We claim:

1. An orthotic brace for a joint of a patient's body, the brace comprising:
   a first brace frame adapted for connection to a first portion of a patient's body on a first side of a joint;
   a second brace frame adapted for connection to a second portion of the patient's body on a second side of the joint; and
   a force element operably connected to at least one of the first and second brace frames imparting a force on one of the first and second brace frames; and
   the force comprises a magnetic force from a magnetic field urging at least one portion of the first and second brace frames to pivot relative to the other brace frame.

2. The orthotic brace of claim 1 wherein the force element comprises a magnet array.

3. The orthotic brace of claim 1 further comprising a pivot connection between the first and second brace frames.

4. The orthotic brace of claim 1 wherein the force on one of the first and second brace frames comprises a predetermined force.

5. The orthotic brace of claim 1 wherein the force on one of the first and second brace frames comprises a force in at least two directions.

6. The orthotic brace of claim 1 further comprising a pivot connection enabling the at least one portion of the first and second brace frames to pivot relative to the other brace frame.

7. The orthotic brace of claim 1 wherein the force is a repelling force.

8. The orthotic brace of claim 1 wherein the force is an attracting force.

9. The orthotic brace of claim 1 wherein the force is a resistance force.

10. An orthotic brace hinge for a joint of a patient's body comprising:
a first hinge element;
a second hinge element;
the first and second hinge elements being operably connected;
the first and second hinge elements having a first and a second force element respectively whereby the first and the second force elements provide a force urging the first and second hinge elements in a pre-determined direction;
the first force element is a first magnet and the second force element is a second magnet;
the first magnet has a first magnetic field and the second magnet has a second magnetic field;
the first magnetic field and the second magnetic field oppose each other;
the force urging the first and second hinge elements is a repelling force;
the first and second hinge elements being operably connected;
the first and second hinge elements being pivotable relative to each other about a pivot; and
the repelling force is capable of imparting a resistance force in the pre-determined direction about the pivot.

11. The orthotic brace hinge of claim 10 wherein one of the first force element and the second force element comprises a magnet array.

12. The orthotic brace hinge of claim 10 wherein the pivot comprises a pivot connection enabling the first hinge element to pivot relative to the second hinge element.

13. The orthotic brace hinge of claim 10 wherein:
the orthotic brace hinge is capable of moving into at least a first flex position and a second flex position; and
the force at the first flex position is different than the force at the second flex position.

14. An orthotic brace comprising:
a first and a second lever operably connected about a pivot; and
the first and second lever being urged in a pre-determined direction by a force element;
the force element comprises a magnet imparting a magnetic force;
the magnetic force comprises an attracting force; and
the attracting force urges movement of the first and the second levers to resist an extension of the first and the second levers.

15. The orthotic brace of claim 14 wherein the force element comprises a magnet array.

16. The orthotic brace of claim 14 further comprising:
the first lever adapted for connection to a first portion of a patient's body on a first side of a joint;
the second lever adapted for connection to a second portion of the patient's body on a second side of the joint; and
the force element operably connected to at least one of the first and second levers imparting a force on one of the first and second levers in a pre-determined direction.

17. The orthotic brace of claim 14 wherein:
the force element further comprises a second magnet imparting a second magnetic force;
the second magnetic force comprises a repelling force; and
the repelling force urges movement of the first and the second levers to resist an extension of the first and the second levers.

18. The orthotic brace of claim 14 wherein:
the first and a second lever are capable of moving into at least a first flex position and a second flex position; and
the force at the first flex position is different than the force at the second flex position.

* * * * *